US005641653A

United States Patent [19]

Struck et al.

[11] Patent Number: 5,641,653

[45] Date of Patent: Jun. 24, 1997

[54] DNA ENCODING *ACTINOBACILLUS PLEUROPNEUMONIAE* HEMOLYSIN

[75] Inventors: Douglas K. Struck; Ryland F. Young, both of College Station, Tex.; Yung-Fu Chang, Ithaca, N.Y.

[73] Assignee: The Texas A&M University System, College Station, Tex.

[21] Appl. No.: 429,273

[22] Filed: Oct. 31, 1989

[51] Int. Cl.[6] .......................... C12N 15/31; C12N 15/63; C12N 1/21; C12P 21/02

[52] U.S. Cl. ...................... 435/69.3; 536/23.7; 536/23.2; 435/320.1; 435/252.3; 435/254.11; 435/325; 935/12; 935/66; 935/72

[58] Field of Search ............................ 424/92, 93, 93 A, 424/93 R; 435/69.1, 172.3, 69.3, 320.1, 252.3, 254.11, 240.1; 536/23.7, 23.2; 935/12, 66, 72

[56] References Cited

PUBLICATIONS

Lo, R.Y.C. et al. 1985 Infect. Immun. vol 50, pp. 667–671.
Koronakis, V. et al. 1987, J. Bacteriol. vol. 169, pp. 1509–1515.
Chang, YF et al. 1987. Infect. Immun. vol. 55 pp. 2348–2354.
Welch, RA. 1987, Infect. Immun. vol. 55, pp. 2183–2190.
Nicaud, J–Metal. 1985, FEBS Lett. vol. 187 pp. 339–344.
Sirois, M. et al. 1989, Abstracts, 89th Annual Meeting of the American Society for Microbiology, p. 98.
Kanp et al. J. Clin Microbiol. 27(6):1187 Jun. '89 (abstract only).
Highlander et al DNA 8:15 (1989).
Lo et al. Infect Imm. 55: 1987 (1987).
Felmlee et al. J. Bact. 163: 88 (1985).
Gunnarsson et al. Am. J. Vet. Res. 40: 1564–1567. 1979.
Young et al. PNAS 80:1194, 1983.
Fedorka–Cray et al., "Efficacy of Hemolysin as a Protective Antigen Against Actinobacillus (Haemophilus) Pleuropneumoniae (APP) Infection in Swine," Abstracts of the Annual Meeting, Abstract No. B–37 (1988).

Strathdee et al., "Cloning, Nucleotide Sequence, and Characterization of Genes Encoding the Secretion Function of the Pastuerella Haemolytica Leukotoxin Determinant," Abstract No. 147554c, p. 149 (1989).

Chang et al., Cloning and Characterization of A Hemolysin Gene from Actinobacillus (Haemophilus) Pleuropneumoniae, DNA, vol. 8, No. 9, pp. 635–647 (1989).

Chang et al., Secretion of the Pasteurella Leukotoxin by Escherichia Coli, FEMS Microbiology Letters 60:169–174 (1989).

Frey and Nicolet, Purification and Partial Characterization of a Hemolysin Produced By Actinobacillus Pleuropneumoniae Type Strain 4074, FEMS Microbiology Letters 55:41–46 (1988).

Maudsley and Kadis, Growth and Hemolysin Production By Haemophilus Pleuropneumoniae Cultivated In A Chemically Defined Medium, Can. J. Microbiol., vol. 32, pp. 801–805 (1986).

Kume et al., Interaction Between Heat–Stable Hemolytic Substance from Haemophilus pleuropneumoniae and Porcine Pulmonary Macrophages In Vitro, Infection and Immunity, vol. 51, No. 2, pp. 563–570 (1986).

Martin et al., Production of RNA–dependent Haemolysin by Haemophilus pleuropneumoniae, Can. J. Microbiol., vol. 31 pp. 456–462 (1985).

Bendixen et al., Toxicity of Haemophilus pleuropneumoniae for Porcine Lung Macrophages, Peripheral Blood Monocytes, and Testicular Cells, Infection and Immunity, vol. 33, No. 3, pp. 673–676 (1981).

*Primary Examiner*—Mary E. Mosher
*Attorney, Agent, or Firm*—Arnold, White & Durkee

[57] ABSTRACT

This invention discloses the DNA sequences coding for the *Actinobacillus pleuropneumonia* hemolysin(s). It further discloses a method of producing the *A. pleuropneumoniae* hemolysin(s) from recombinant cells. It also provides a method of using the hemolysin(s) antigen as a protective immunogen against porcine pleuropneumonia.

17 Claims, 6 Drawing Sheets

```
-260              -240              -220              -200              -180
GAACGTGAAGAGCCATTACCCAACAACAAAAAAGCAATGGCTTAACCATTACAGAACGTTGGTACAAAAAATTTTACAGGAAAATGATGG
          -160              -140              -120              -100
ATAGTCCTTAACAAAAATTAATGTTTTATTTCCTATAAAACATCCGATCAGTATTATTTTTGATTAAAAAAAGAACAAACAGATCATGAC
   -80               -60               -40         ^^^^^^ -20         1
AAACGTTGCCTTGTTTTCCTTCACAAAAATATTATGGTTTTTATTTAGAATAAATTATCTATATTCATTTTTTAGGGAATGGGAGGGAT -> appC
    ^^^^^^                  ^^^^^^                  ^^^^^^   ^^^^^^                      M
          20                40                60                80
GATGCTAAAAAATTTTAACGTATTGGGACAAATTGCTTGGTTATGGGCAAATTCTCCAATGCACCGAAATTGGTCAGTTTCACTGTTAAT
 M  L  K  N  F  N  V  L  G  Q  I  A  W  L  W  A  N  S  P  M  H  R  N  W  S  V  S  L  L  M
  100               120               140               160               180
GAAGAATGTTATTCCTGCAATTGAAAATGACCCAATATTTGTTACTGTTGATGATGGTTTTCCTATTGCATATTGCAGTTCCCGGAAATT
 K  N  V  I  P  A  I  E  N  D  P  I  F  V  T  V  D  D  G  F  P  I  A  Y  C  S  S  R  K  L
          200               220               240               260
AACTCTAGAGAGTGAGGCTCGCTATGTAAAGGACACCAATTCATTAAAAATAGATGATTGGAATGCAGGAGATCGTATATGGATCATTGA
 T  L  E  S  E  A  R  Y  V  K  D  T  N  S  L  K  I  D  D  W  N  A  G  D  R  I  W  I  I  D
  280               300               320               340               360
TTGGATTGCCCCATTCGGGGATTCATCTCTATTGTATAAACATATGAGACAACGTTTTCCATACGATATTGGAAGGGCAATTAGAATCTA
 W  I  A  P  F  G  D  S  S  L  L  Y  K  H  M  R  Q  R  F  P  Y  D  I  G  R  A  I  R  I  Y
          380               400               420               440
TCCTAGCAAAAAAGATACTGGAAAAATCATATATTTAAAAGGAGGAAAAATAACAAAAAAAGTAGCTGAAAAGACATTTCTTCAGTATGA
 P  S  K  K  D  T  G  K  I  I  Y  L  K  G  G  K  I  T  K  K  V  A  E  K  T  F  L  Q  Y  E
  460               480               500               520               540
GCAAGAGTTAATAACAGCTCTACAATAATATCTTTAAATGATCAATTATATAAAGGAGACTCTTTTATGTCAAAAATCACTTTGTCATCA -> appA
 Q  E  L  I  T  A  L  Q  *                                            M  S  K  I  T  L  S  S
          560               580               600               620
TTAAAATCGTCCTTACAACAAGGATTGAAAAATGGGAAAAACAAGTTAAATCAAGCAGGTACAACACTGAAGAATGGTTTAACTCAAACT
 L  K  S  S  L  Q  Q  G  L  K  N  Q  K  N  K  L  N  Q  A  G  T  T  L  K  N  G  L  T  Q  T
  640               660               680               700               720
GGTCATTCTCTACAGAATGGGGCTAAAAAATTAATCTTATATATTCCTCAAGGCTATGATTCGGGTCAAGGAAATGGAGTTCAAGATTTA
 G  H  S  L  Q  N  G  A  K  K  L  I  L  Y  I  P  Q  G  Y  D  S  G  Q  G  N  G  V  Q  D  L
```

FIG. 1A

```
          740                 760                 780                 800
GTTAAAGCTGCTAATGATTTAGGTATTGAAGTATGGCGAGAAGAACGCAGCAATTTGGACATTGCAAAAACTAGCTTTGATACAACTCAG
V  K  A  A  N  D  L  G  I  E  V  W  R  E  E  R  S  N  L  D  I  A  K  T  S  F  D  T  T  Q
     820                 840                 860                 880                 900
AAAATTCTAGGTTTTACTGATAGAGGAATTGTATTATTTGCACCTCAGCTAGATAATTTATTAAAGAAGAATCCTAAAATTGGCAATACA
K  I  L  G  F  T  D  R  G  I  V  L  F  A  P  Q  L  D  N  L  L  K  K  N  P  K  I  G  N  T
          920                 940                 960                 980
TTAGGAAGTGCTTCTAGCATCTCACAAAATATAGGTAAAGCCAATACTGTATTAGGTGGTATTCAATCTATTTTAGGATCTGTTTTATCT
L  G  S  A  S  S  I  S  Q  N  I  G  K  A  N  T  V  L  G  G  I  Q  S  I  L  G  S  V  L  S
    1000                1020                1040                1060                1080
GGAGTAAATCTGAATGAATTACTTCAAAATAAAGATCCTAATCAATTAGAACTTGCAAAAGCAGGGCTAGAACTGACTAATGAATTAGTT
G  V  N  L  N  E  L  L  Q  N  K  D  P  N  Q  L  E  L  A  K  A  G  L  E  L  T  N  E  L  V
         1100                1120                1140                1160
GGTAATATTGCTAGCTCGGTGCAAACTGTAGATGCATTTGCAGAACAAATATCTAAACTAGGTTCACATTTACAGAATGTGAAAGGATTA
G  N  I  A  S  S  V  Q  T  V  D  A  F  A  E  Q  I  S  K  L  G  S  H  L  Q  N  V  K  G  L
    1180                1200                1220                1240                1260
GGAGGATTGAGTAATAAATTACAAAATCTACCAGATCTAGGAAAAGCAAGTTTAGGTTTGGACATTATCTCTGGTTTACTTTCTGGAGCA
G  G  L  S  N  K  L  Q  N  L  P  D  L  G  K  A  S  L  G  L  D  I  I  S  G  L  L  S  G  A
         1280                1300                1320                1340
TCTGCAGGTCTCATTTTAGCAGATAAAGAGGCTTCAACAGAAAAGAAAGCTGCCGCAGGTGTAGAATTTGCTAACCAAATTATAGGTAAT
S  A  G  L  I  L  A  D  K  E  A  S  T  E  K  K  A  A  A  G  V  E  F  A  N  Q  I  I  G  N
```

FIG.1A-1

```
1360              1380              1400              1420              1440
GTAACAAAAGCGGTCTCATCTTACATTCTTGCCCAACGAGTCGCTTCAGGTTTGTCTTCAACTGGTCCTGTCGCTGCATTAATCGCATCT
V  T  K  A  V  S  S  Y  I  L  A  Q  R  V  A  S  G  L  S  S  T  G  P  V  A  A  L  I  A  S
         1460              1480              1500              1520
ACAGTTGCACTAGCTGTTAGCCCTCTTTCATTCTTAAATGTAGCTGATAAGTTTAAACAAGCTGATTTAATCAAATCATATTCTGAACGC
T  V  A  L  A  V  S  P  L  S  F  L  N  V  A  D  K  F  K  Q  A  D  L  I  K  S  Y  S  E  R
1540              1560              1580              1600              1620
TTCCAAAAATTAGGATATGATGGAGATCGTTTATTAGCTGATTTTCACCGTGAGACAGGAACTATTGATGCTTCTGTAACAACAATTAAC
F  Q  K  L  G  Y  D  G  D  R  L  L  A  D  F  H  R  E  T  G  T  I  D  A  S  V  T  T  I  N
         1640              1660              1680              1700
ACTGCTTTAGCAGCTATCTCCGGTGGAGTTGGAGCTGCAAGCGCGGGTTCTCTAGTCGGAGCTCCAGTTGCGTTACTCGTTGCTGGTGTT
T  A  L  A  A  I  S  G  G  V  G  A  A  S  A  G  S  L  V  G  A  P  V  A  L  L  V  A  G  V
1720              1740              1760              1780              1800
ACGGGACTTATTACAACTATTCTAGAATATTCTAAACAAGCCATGTTTGAACATGTTGCAAATAAGGTTCATGACAGAATAGTTGAATGG
T  G  L  I  T  T  I  L  E  Y  S  K  Q  A  M  F  E  H  V  A  N  K  V  H  D  R  I  V  E  W
         1820              1840              1860              1880
GAGAAAAAACATAATAAAAACTATTTTGAGCAAGGTTATGATTCTCGTCATTTAGCTGATTTACAAGACAATATGAAGTTTCTTATCAAT
E  K  K  H  N  K  N  Y  F  E  Q  G  Y  D  S  R  H  L  A  D  L  Q  D  N  M  K  F  L  I  N
1900              1920              1940              1960              1980
TTAAATAAAGAACTTCAGGCTGAACGCGTAGTAGCTATTACCCAACAAAGATGGGATAACCAAATTGGAGACCTAGCGGCAATTAGCCGT
L  N  K  E  L  Q  A  E  R  V  V  A  I  T  Q  Q  R  W  D  N  Q  I  G  D  L  A  A  I  S  R
         2000              2020              2040              2060
AGAACGGATAAAATTTCCAGTGGAAAAGCTTATGTGGATGCTTTTGAGGAGGGGCAACACCAGTCCTACGATTCATCCGTACAGCTAGAT
R  T  D  K  I  S  S  G  K  A  Y  V  D  A  F  E  E  G  Q  H  Q  S  Y  D  S  S  V  Q  L  D
2080              2100              2120              2140              2160
AACAAAAACGGTATTATTAATATTAGTAATACAAATAGAAAGACACAAAGTGTTTTATTCAGAACTCCATTACTAACTCCAGGTGAAGAG
N  K  N  G  I  I  N  I  S  N  T  N  R  K  T  Q  S  V  L  F  R  T  P  L  L  T  P  G  E  E
         2180              2200              2220              2240
AATCGGGAACGTATTCAGGAAGGTAAAAATTCTTATATTACAAAATTACATATACAAAGAGTTGACAGTTGGACTGTAACAGATGGTGAT
N  R  E  R  I  Q  E  G  K  N  S  Y  I  T  K  L  H  I  Q  R  V  D  S  W  T  V  T  D  G  D
2260              2280              2300              2320              2340
GCTAGCTCAAGCGTAGATTTCACTAATGTAGTACAACGAATCGCTGTGAAATTTGATGATGCAGGTAACATTATCGAATCTAAAGATACT
A  S  S  S  V  D  F  T  N  V  V  Q  R  I  A  V  K  F  D  D  A  G  N  I  I  E  S  K  D  T
```

FIG. 1B

```
          2360          2380          2400          2420
AAAATTATCGCAAATTTAGGTGCTGGTAACGATAATGTATTTGTTGGGTCAAGTACTACCGTTATTGATGGCGGGGACGGACATGATCGA
K  I  I  A  N  L  G  A  G  N  D  N  V  F  V  G  S  S  T  T  V  I  D  G  G  D  G  H  D  R
    2440          2460          2480          2500          2520
GTTCACTACAGTAGAGGAGAATATGGCGCATTAGTTATTGATGCTACAGCCGAGACAGAAAAAGGCTCATATTCAGTAAAACGCTATGTC
V  H  Y  S  R  G  E  Y  G  A  L  V  I  D  A  T  A  E  T  E  K  G  S  Y  S  V  K  R  Y  V
          2540          2560          2580          2600
GGAGACAGTAAAGCATTACATGAAACAATTGCCACCCACCAAACAAATGTTGGTAATCGTGAAGAAAAAATTGAATATCGTCGTGAAGAT
G  D  S  K  A  L  H  E  T  I  A  T  H  Q  T  N  V  G  N  R  E  E  K  I  E  Y  R  R  E  D
    2620          2640          2660          2680          2700
GATCGTTTTCATACTGGTTATACTGTGACGGACTCACTCAAATCAGTTGAAGAGATCATTGGTTCACAATTTAATGATATTTTCAAAGGA
D  R  F  H  T  G  Y  T  V  T  D  S  L  K  S  V  E  E  I  I  G  S  Q  F  N  D  I  F  K  G
          2720          2740          2760          2780
AGCCAATTTGATGATGTGTTCCATGGTGGTAATGGTGTAGACACTATTGATGGTAACGATGGTGACGATCATTTATTTGGTGGCGCAGGC
S  Q  F  D  D  V  F  H  G  G  N  G  V  D  T  I  D  G  N  D  G  D  D  H  L  F  G  G  A  G
    2800          2820          2840          2860          2880
GATGATGTTATCGATGGAGGAAACGGTAACAATTTCCTTGTTGGAGGAACCGGTAATGATATTATCTCGGGAGGTAAAGATAATGATATT
D  D  V  I  D  G  G  N  G  N  N  F  L  V  G  G  T  G  N  D  I  I  S  G  G  K  D  N  D  I
```

FIG. 1B-1

```
          2900                2920                2940                2960
TATGTCCATAAAACAGGCGATGGAAATGATTCTATTACAGACTCTGGCGGACAAGATAAACTGGCATTTTCGGATGTAAATCTTAAAGAC
Y  V  H  K  T  G  D  G  N  D  S  I  T  D  S  G  G  Q  D  K  L  A  F  S  D  V  N  L  K  D
    2980                3000                3020                3040                3060
CTCACCTTTAAGAAAGTAGATTCTTCTCTCGAAATCATTAATCAAAAAGGAGAAAAAGTTCGTATTGGGAATTGGTTCTTAGAAGATGAT
L  T  F  K  K  V  D  S  S  L  E  I  I  N  Q  K  G  E  K  V  R  I  G  N  W  F  L  E  D  D
          3080                3100                3120                3140
TTGGCTAGCACAGTTGCTAACTATAAAGCTACGAATGACCGAAAAATTGAGGAAATTATTGGTAAAGGAGGAGAACGTATTACATCAGAA
L  A  S  T  V  A  N  Y  K  A  T  N  D  R  K  I  E  E  I  I  G  K  G  G  E  R  I  T  S  E
    3160                3180                3200                3220                3240
CAAGTTGATAAACTGATTAAGGAGGGTAACAATCAAATCTCTGCAGAAGCATTATCCAAAGTTGTGAATGATTACAATACGAGTAAAGAT
Q  V  D  K  L  I  K  E  G  N  N  Q  I  S  A  E  A  L  S  K  V  V  N  D  Y  N  T  S  K  D
          3260                3280                3300                3320
AGACAGAACGTATCTAATAGCTTAGCAAAATTGATTTCTTCAGTCGGGAGCTTTACGTCTTCCTCAGACTTTAGGAATAATTTAGGAACA
R  Q  N  V  S  N  S  L  A  K  L  I  S  S  V  G  S  F  T  S  S  S  D  F  R  N  N  L  G  T
    3340                3360                3380                3400                3420
TATGTTCCTTCATCAATAGATGTCTCGAATAATATTCAATTAGCTAGAGCCGCTTAATATTCAAATCATAGCAATCCTATGGTGTAAATT
Y  V  P  S  S  I  D  V  S  N  N  I  Q  L  A  R  A  A  *
          3440                3460                3480                3500
ATAGGATTGTTATTTTTTTAAAGGAGAAGTTATGGAACCCAATAAAAATAAGGATCTTGGTTTAGCTGCACTTAAAATTCTTGCTCAATA
                                 M  E  P  N  K  N  K  D  L  G  L  A  A  L  K  I  L  A  Q  Y
    3520                3540                3560
TCATAATATTTCAGTCAATCCCGAAGAATTAAAACATAAATTTGATCTAGA
 H  N  I  S  V  N  P  E  E  L  K  H  K  F  D  L
```

FIG.1C

DNA ENCODING *ACTINOBACILLUS PLEUROPNEUMONIAE* HEMOLYSIN

The United States Government may have certain rights to this invention pursuant to research contract USDA No. 6146-01.

BACKGROUND OF THE INVENTION

The present invention relates to the cloning of the gene expressing antigens of *Actinobacillus pleuropneumonia* (*A. pleuropneumoniae*). It further relates to a method of producing these antigens and the use of the antigens to vaccinate pigs against porcine pleuropneumonia.

Haemophilus pleuropneumonia of swine is a highly contagious respiratory disease caused by the gram-negative bacterium, *A. pleuropneumoniae*. In recent years, partly because of the trend toward confinement and intensified production, there has been a significant increase in the incidence of the disease and it is now a major cause of economic loss to the swine industry. During outbreaks of the acute disease the mortality rate can reach 100% among piglets and 25% among feeder pigs. Infected pigs may develop acute local extensive pneumonia accompanied by a fibrinous pleuritis or chronic localized pulmonary necrosis is with pleuritic adhesions. Eight serotypes of *A. pleuropneumoniae* have been identified but serotype 5 is by far the most prevalent.

It appears that one of the virulence factors of *A. pleuropneumoniae* is a secreted cytotoxin. This is supported by the fact cell-culture supernatants from *A. pleuropneumoniae* have been shown to be cytotoxic for porcine alveolar macrophages and peripheral monocytes (Bendixin et al., *Infect. Immun.* 33, 673–676 (1981)). Additionally, sonicated bacteria and sterile culture supernatants have been reported to induce localized pneumonia which is similar to pneumonia observed in naturally infected pigs (Rosendal et al., *Proc. Int. Pig. Vet. Soc. Congr.* 5: 221 (1980)).

It is believed that the *A. pleuropneumoniae* cytotoxin is an extracellular hemolysin/s produced by most if not all *A. pleuropneumoniae* serotypes. The nature of the hemolysin/s is poorly understood. It has been reported that the various serotypes of *A. pleuropneumoniae* produce either heat-stable carbohydrates (Kume et al., *Infect. Immun.* 51, 563–570 (1986)) or heat labile proteins (Maudsely et al., *Can. J. Microbiol.* 32, 801–805 (1986)). It has also been reported that the hemolysins of *A. pleuropneumoniae* serotypes 1, 2, 3, 5, 6,and 7 require RNA (Martin et al., *Can. J. Microbiol.* 31, 456–462 (1985)). To date, only two hemolysins have been characterized, a heat stable hemolysin from serotype 2 (Kume et al., *Infect. Immun.* 51, 563–570 (1986)) and a 105 KD polypeptide secreted by serotype 1 (Frey et al., *Infect. Immun.* 56, 2570–2575 (1988)). The amino acid sequence of any *A. pleuropneumoniae* hemolysin(s) has been unknown until the current invention.

There is currently no commercially available vaccine for porcine pleuropneumonia. Immunizations have been attempted using heat killed or formalin fixed bacteria but the efficiency of these immunogens has not been clinically proven. It is expected that the *A. pleuropneumoniae* hemolysin(s) can be used as a protective immunogen for pigs against porcine pleuropneumonia.

SUMMARY OF THE INVENTION

In its most general and overall scope this invention discloses DNA sequences encoding for *A. pleuropneumoniae* hemolysin antigen. It further provides for recombinant vectors and recombinant cells containing the DNA sequences and for a method for producing *A. pleuropneumoniae* hemolysin antigen utilizing the recombinant cells. This invention further discloses the use of the *A. pleuropneumoniae* hemolysin antigen to vaccinate pigs against porcine pleuropneumonia.

More particularly, this invention provides for DNA sequences which encode for the appCA amino acid sequence or the appA amino acid sequence shown in FIG. 1 or polypeptides having substantially the same amino acid sequences and biological activity. In a specific embodiment the invention provides for DNA sequences for the appCA and appA nucleotide sequences shown in FIG. 1 or allelic variations thereof. The invention further provides for DNA sequences which encode for an antigenic determinant of *A. pleuropneumoniae* hemolysin. In the preferred embodiment it provides for the DNA sequence corresponding to that contained in ATCC Deposit No. 68135.

The invention further provides for recombinant vectors containing the above-described DNA sequences. More particularly it provides that the recombinant vectors are bacterial plasmids and that the DNA sequences are operatively linked to a strong promoter sequence. Additionally, it provides for recombinant cells containing the above-described DNA sequences, most preferably bacterial cells. It further provides for an *A. pleuropneumoniae* antigen encoded by the appA gene or an allelic variation thereof or a polypeptide having substantially the same amino acid sequence and biological activity.

*A. pleuropneumoniae* hemolysin antigen can be produced by culturing and processing the recombinant cells described above, and this invention provides for a method of producing the *A. pleuropneumoniae* antigen. It further provides for a composition containing the antigen and for a method for using the antigen as a vaccine against porcine pleuropneumonia.

BRIEF DESCRIPTION OF THE DRAWINGS

FIG. 1A–1C depicts the nucleotide sequence of the appCA region and the predicted amino acid sequences of the appC and appA proteins. Promoter like regions proximal to the appC gene are indicated by the symbol ô directly beneath the nucleotide sequences. Potential ribosome binding sequences preceding appC, appA and immediately after appA are indicated by underlining.

Figure 2:
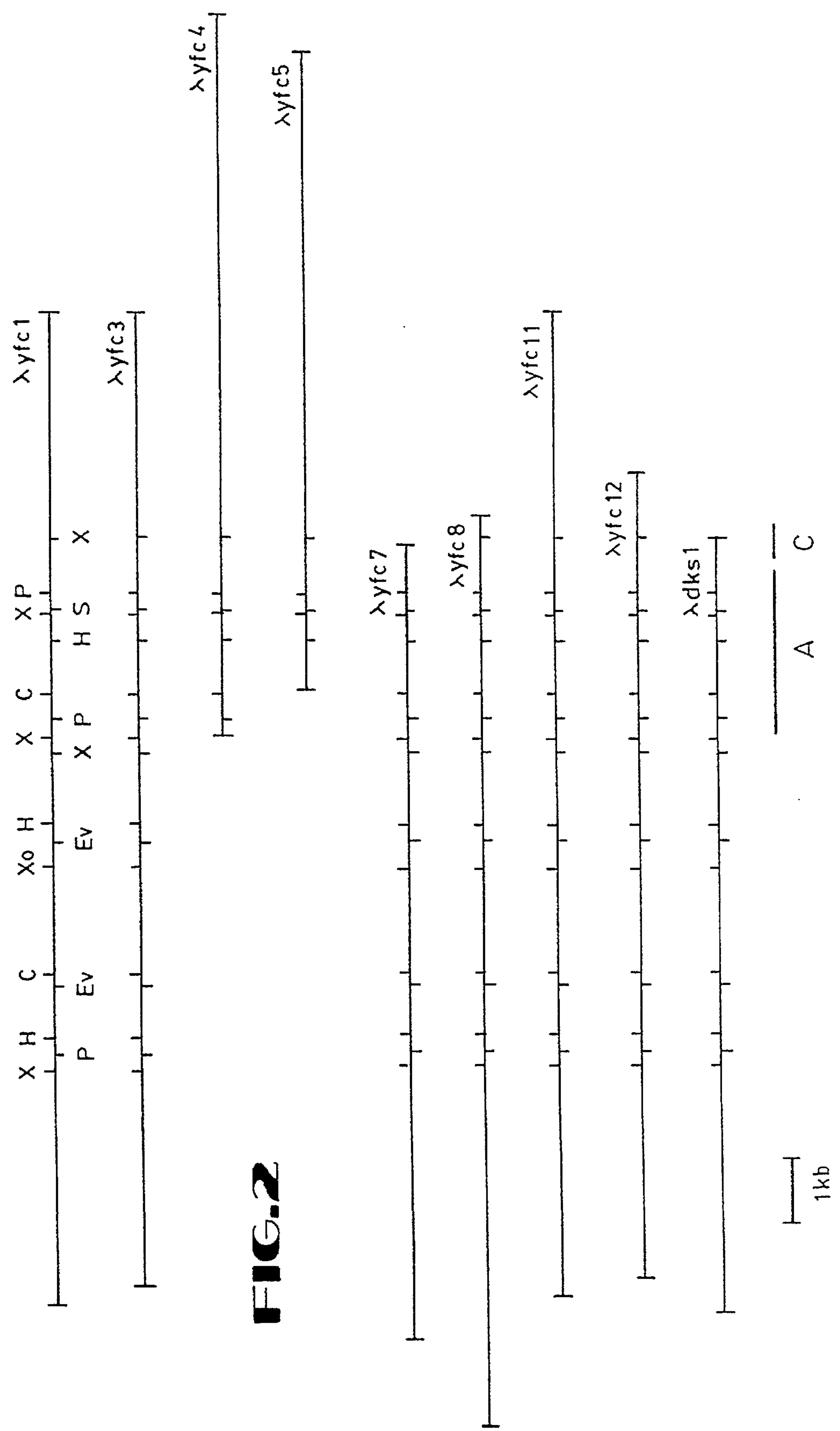

The start of the open reading frame for appC is indicated at position 1 and the start of the open reading frame for appA is indicated at nucleotide position 519.

FIG. 2 depicts the restriction maps of the *A. pleuropneumoniae* hemolysin clones. EcoR1 sites derived from the vector flank the inserts of each clone. Except for λyfc5 each clone expressed a 110 kD polypeptide detected by Western blotting. The locations of the two open reading frames designated appC and appA found by sequence analysis are indicated: C, ClaI; Ev, EcoRV; H, HindIII; P, PstI; S, SacI; X, SbaI; Xo, XhoI.

DETAILED DESCRIPTION OF THE INVENTIONS

The DNA sequences and *A. pleuropneumoniae* hemolysin antigens of this invention provide an efficient and economical means for producing an effective vaccine for immunizing pigs against porcine pleuropneumonia. The DNA sequences provided for in this invention can be utilized in various expression systems to produce high levels of *A. pleurop-*

*neumoniae* hemolysin antigen. In a preferred method the DNA sequences are positioned downstream from strong bacterial promoters to allow the highest possible yield of material. The antigen produced by the bacteria can then be isolated and purified and introduced into pigs as a vaccine against pleuropneumonia.

The DNA sequences isolated and cloned in the current invention encode for the *A. pleuropneumonia* hemolysin. They more specifically encode for a 110 kD hemolysin from *A. pleuropneumonia* serotype 5. The most preferred embodiments of the current invention are the DNA sequences shown in FIG. 1. Of course it will be recognized by those skilled in the art that the DNA sequences may vary due to the degeneracy of the genetic code. All DNA sequences which code for the *A. pleuropneumoniae* antigens shown in FIG. 1 are included in this invention. Additionally, it will be recognized by those skilled in the art that allelic variations may occur in the DNA sequences which will not significantly change the antigenic activity or the amino acid sequence of the polypeptides for which the DNA sequences code. These allelic variations are also covered by this invention.

The current invention provides for two different genes designated appC and appA. These encode polypeptides of 159 and 957 amino acids respectively. The appA gene codes for a protein designated appA antigen which has no hemolytic activity. Expression of both the appA and appC genes is necessary for the normal hemolytic activity of the *A. pleuropneumoniae* hemolysin. The protein produced by these two genes is designated the appCA antigen. Both the appCA and appA antigens produce an antibody response from the antibodies to the natural *A. pleuropneumoniae* hemolysin. It is expected that both the appA and the appCA antigens can be utilized to elicit an immune response in a pig which will prevent pleuropneumonia. Therefore the DNA sequences coding for both the appCA and the appA antigen is covered by this invention.

Furthermore, it should be noted that amino acid sequences may exist or be constructed which are substantially similar to the natural *A. pleuropneumoniae* hemolysin polypeptide shown in FIG. 1 and which perform substantially the same hemolytic and antigenic functions. It will be recognized by those skilled in the art that amino acid sequence changes can be made that will, for example, increase or decrease the biological activity of a specific peptide without changing the nature of its function. DNA sequences coding for these peptides are also covered by this invention.

It will also be obvious to those skilled in the art that the appA and appCA antigens may contain various antigenic determinants (epitopes) which can be recognized by the natural antibodies produced to *A. pleuropneumoniae* hemolysin. These antigenic determinants could be used either alone or as haptens to elicit an immune response in a pig which would protect it against pleuropneumonia. One method of utilizing the hapten would be to couple it to a carrier such as albumin. This invention further covers any DNA sequence encoding for an amino acid sequence containing an antigenic determinant of *A. pleuropneumoniae* hemolysin. A preferred embodiment is a DNA sequence coding for a sequence of amino acids as shown in FIG. 1 or a substantially similar sequence which contains an antigenic determinant of *A. pleuropneumoniae* hemolysin.

Additionally, this invention provides for antigenic polypeptides which are not produced naturally by *A. pleuropneumoniae*. As noted above, the appA antigen coded for by the appA gene is not hemolytic and would not naturally be produced by *A. pleuropneumoniae*. The appA antigen, however does elicit an immune response and can be used as a vaccine. Therefore, this invention covers the appA antigen which is coded for by the appA gene. For the purposes of the invention the term *A. pleuropneumoniae* hemolysin antigen includes *A. pleuropneumoniae* hemolysin, the appA antigen, the appCA antigen and any amino acid sequence which contains an antigenic determinant of *A. pleuropneumoniae* hemolysin.

The genes for the *A. pleuropneumoniae* hemolysin are cloned by first isolating *A. pleuropneumoniae* DNA from the various serotype strains or from strains isolated from Actinobacillus infected pigs. By way of illustration the inventors have employed an *A. pleuropneumoniae* serotype 5. This was chosen because it is the most prevalent of the serotypes and one of the most virulent. However, virtually any strain which is capable of eliciting porcine pleuropneumonia may be employed. In the current invention it is preferable to prepare a genomic library of the *A. pleuropneumoniae* chromosomal DNA. Various methods for preparing such libraries are available and it will be evident to one skilled in the art that various recombinant vectors and restriction enzymes may be used in this process. Preferably a digest of the *A. pleuropneumoniae* chromosomal DNA will be cloned into a bacteriophage library using standard techniques.

Because the serotype 5 hemolysin had not been characterized or sequenced a method to isolate and select the hemolysin gene had to be developed. It has become apparent that a number of gram-negative pathogenic organisms secrete high molecular weight (105–110 KD) lytic toxins which are immunologically and genetically related to the hemolysin of *Escherichia coli* (Chang et al., *FEMS Lett.*, 60, 169–174 (1989), and Koranakis, et al., J. Bacteriol. 169, 1509–1515 (1987)). To determine if the secreted hemolysin of *A. pleuropneumoniae* is a member of the RTX cytotoxin family, culture supernatants from *P. haemolytica, A. pleuropneumoniae* and an *E. coli* strain carrying pSF4000 were analyzed by Western blot using antiserum raised against *P. haemolytica* leukotoxin. A cross-reacting polypeptide species of $M_r$=110,000, slightly larger than the apparent molecular weight of the leukotoxin and nearly identical to the *E. coli* hemolysin was detected.

This indicated that the *A. pleuropneumoniae* hemolysin is in the same family as the *P. haemolytica* leukotoxin. Therefore, a portion of the published sequence of the 1ktCA gene from *P. haemolytica* was used as a probe to isolate the desired clones. Additionally, in the present invention antibodies to *A. pleuropneumoniae* hemolysin were prepared and used for immunologic screening of the bacteriophage library. These screening methods were performed using standard techniques. Placques which give positive signals are picked, rescreened and amplified. The restriction fragments from selected phage inserts can then be sequenced by various methods including Maxam and Gilbert and the di-deoxy chain termination method of Sanger.

In the current invention antibody screening identified a single positive clone (see FIG. 2). Screening of the same library with DNA probes derived from *P. haemolytica* identified eight clones that overlapped each other and the clone isolated by antibody screening (see FIG. 2). The DNA cloned in the current invention was a 3.8 kb fragment containing the entire reading frame for the appA antigen and also the reading frame for the smaller appC protein which activates the toxin protein. These two genes together are the appCA genes which encode the entire 110 kD appCA antigen with hemolytic activity. The nucleotide sequence of the appCA region and the predicted amino acid sequences of the appC and appA proteins are shown in Table 1.

The DNA fragment containing the appCA genes can then be subcloned into an appropriate recombinant vector such as a plasmid or a bacteriophage viral vector. Those skilled in the art will recognize that there are numerous possible vectors which may be utilized such as pBR322, the pAR series, pKK223-3 and the pUR series, and even more numerous techniques for the construction of these recombinant vectors. Some of the parameters surrounding the choice of vector will include the type of expression system to be utilized and the size of the DNA insert. Because the appCA genes are bacterial genes and the preferred expression vector is a bacterial cell the preferred recombinant vector is a bacterial vector, most preferably a bacterial plasmid. In the current invention the appCA regions from bacteriophage clones λyfc7 and λyfc8 were subcloned into the vector pHG165.

The recombinant vector is then introduced into the chosen expression system by a method appropriate to that system. While a bacterial expression system is most commercially viable for the current invention, a eukaryotic system could also be utilized. Examples of appropriate expression systems include *E. coli* JM103, *E. coli* C600, *E. coli* C04 and *E. coli* DH20. The expression system used in the current invention was *E. coli* TB1.

Although, appCA genes can be expressed in the recombinant system using the natural *A. pleuropneumoniae* promoter it is preferable that appCA genes be placed downstream from an appropriate strong promoter and/or amplifier gene. The type of promotor and/or amplifier will depend on the recombinant vector and expression system. Preferred promoters in the current invention are strong bacterial promoters such as the lac or tryp promoters. Examples of other promoters which could be used include the T7RNA polymerase promoter and tac promoter. This will provide for considerably higher levels of expression of antigen. The recombinant vectors containing the DNA sequences described earlier and the recombinant cells containing these DNA sequences which can be utilized to produce *A. pleuropneumoniae* antigens are covered in this invention.

The cells are cultured under conditions which allow production of the antigen. It will be obvious to those skilled in the art that there are many different methods, media, and inducing conditions which can be used depending upon the host strain and the recombinant plasmid. The antigen is then isolated from the culture mixture. In the current invention, the appA and the appCA antigens are expected to form insoluble inclusion bodies due to high level expression in the *Escherichia coli* host. This phenomenon has been shown to occur with many overproduced proteins (Schoner, et al., *Bio/Technology* 3: 151–154 (1985)). Purification of inclusion bodies is relatively simple. For example, bacterial cells are disrupted by sonication or passage through a French pressure cell. Inclusion bodies are then collected by centrifugation and contaminating bacterial debris is removed by extraction with low concentrations of urea and a nonionic detergent. The inclusion bodies are then solubilized with the denaturing agent guanidine hydrochloride and the antigen is renatured by reducing the guanidine hydrochloride concentration by dilution. The above method is only one standard technique of purifying proteins expressed by *E. coli*. This method and other methods of producing an *A. pleuropneumoniae* antigen are covered by the current invention.

A therapeutically active amount of the *A. pleuropneumoniae* antigen may be mixed with a suitable carrier to prepare a vaccine. Those skilled in the art will recognize that many suitable carriers exist and all such compositions are covered by the current invention. A preferred composition would include 0.5–1.0 mg. of crude antigen in an incomplete adjuvant. The *A. pleuropneumoniae* antigens in either purified form or in a composition may then be introduced into a pig to vaccinate the animal against pleuropneumonia.

EXAMPLES

Meterials and Methods

Deposit of Recombinant Plasmid Containing appCA Genes

The preferred recombinant vector containing the appCA genes, plasmid pYFC37, was deposited with the American Type Culture Collection on Oct. 19, 1989 and given Accession No. 68135.

Bacterial Strains, Media, and Culture Conditions

*A. pleuropneumoniae* serotype 5 was obtained courtesy of C. Pijoan, University of Minnesota, St. Paul. *A. pleuropneumoniae* cultures were grown in brain heart infusion broth (BHI, Difco Laboratories) supplemented with 0.1% NAD. LB, Luria Broth (Miller, *Experiments in Molecular Genetics*, p. 433 (1972)), was used for culturing all *E. coli* strains. The bacteriophage cloning vector Lambda-Dash was obtained from Strategene (La Jolla, Calif.). The initial host for the recombinant bacteriophage library was P2392, a P2 lysogen of *E. coli* strain LE392.

General Methods

Although the methodology described below is believed to contain sufficient detail to enable one skilled in the art to practice the present invention, the commercially available technical manual entitled *Molecular Cloning*, Maniatis et al., Cold Spring Harbor Laboratory, Cold Spring Harbor, N.Y., may provide additional details used to assist practice of some aspects of the invention. Accordingly, this manual is incorporated herein by reference. While the following cloning systems have been employed by the present inventors by way of illustration and necessity given the lack of knowledge regarding the *A. pleuropneumoniae* hemolysins it will be recognized that virtually any cloning system may be employed now that the nucleotide sequence has been disclosed.

Preparation of Anti-*H. Pleuropneumoniae* Serum in Pigs

The antiserum against *A. pleuropneumonia* was prepared as described by Gunnarsson (*Am. J. Vet. Res.* 40, p. 1564 (1979)). Serum from these vaccinated pigs was shown to neutralize the hemolysin in culture supernatants from *A. pleuropneumoniae* serotype 5.

Affinity Purification of Anti-Hemolysin Antisera

A 500 ml culture of *A. pleuropneumoniae* was grown to early stationary phase in BHI supplemented with 0.1% NAD. The cell free culture supernatant was concentrated 10 fold by ultrafiltration and the hemolysin protein (approximately 1 mg) was precipitated with five volumes of cold acetone. The precipitate was redissolved by boiling in SDS-PAGE sample buffer and subjected to preparative SDS-PAGE. The 105 kD hemolysin band was visualized using 4M sodium acetate (Hunkapiller et al., *Methods in Enzymol.* 91, p. 227 (1983)), excised, and the hemolysin protein was electrophoretically transferred to nitrocellulose (Towbin et al., *Proc. Natl. Acad. Sci. U.S.A.* 76, p. 4350 (1979)). After transfer, the nitrocellulose strip was incubated in TBST (20 mM Tris-HC1,pH 7.5, 150 mM NaC1, 0.05% Tween 20) containing 3% gelatin. Next, the strip was incubated in 5 ml of the same buffer containing 100 1 of the crude anti-*A. pleuropneumoniae* sera for four hours at room temperature followed by four washes with TBST to remove unbound antibody. Specifically bound antibody was eluted by a five minute incubation in 5 ml of 0.1M glycine, pH 2.5 containing 0.1 mg/ml bovine serum albumin. The eluate was immediately neutralized with 1M Tris base.

Construction of a Clone Bank of *A. Pleuropneumoniae* DNA in Lambda-Dash

*A. pleuropneumonia* chromosomal DNA was purified according to Silhavey et al. (*Experiments with Gene Fusion*, p. 89, Cold Spring Harbor (1984)) and partially digested with SAU 3A. The digested DNA was fractionated by sedimentation through a 10–40% sucrose gradient (Maniatis et al., *Molecular Cloning: A laboratory Manual*, pp. 275–277 (1982)), and fractions containing 9 to 20 kbp fragments, as judged by agarose gel electrophoresis, were pooled and concentrated by alcohol precipitation to a final concentration of 100 μg/ml. Lambda-Dash was cleaved with Bam HI and treated with alkaline phosphatase to remove terminal phosphates. After phenol extraction and concentration by ethanol precipitation, the vector DNA was mixed with size selected *A. pleuropneumoniae* DNA at a molar ratio of 1:4 and treated with T4 DNA ligase for 18 hours at 15° C. The ligated DNA mixture was packaged into lambda particles using a commercially available in vitro packaging kit (Gigapack plus, Stratagene, La Jolla, CALIF.). The phage titers were determined on P2392. Recombinant phage were amplified as plate stocks on P2392.

Screening Phage Libraries for the *A. Pleuropneumoniae* Hemolysin Gene

The bacteriophage library was screened using the affinity purified antihemolysin antibody and by hybridization using a probe containing the 1ktCA genes from *P. haemolytica*. For antibody screening, the library was plated on 150×10mm plates at a density of 5000 plaques per plate. Plaques were transferred to nitrocellulose and each filter was probed with 1 ml of the affinity purified antibody using standard procedures (Huynh, et al., *In DNA Cloning: A Practical Approach*, Vol. I, p. 49, Glover Ed. (1985)). Positive plaques were identified with an alkaline phosphatase conjugated goat anti-swine IgG (Kirkegaard and Perry Laboratories, Gaithersburg, MD) second antibody followed by color development with the substrates nitro blue tetrazolium (NBT) and 5-bromo-4-chloro-3-indolyl phosphate (BCIP) as described (Hawkes et al., Anal. Biochem., 119, p. 142 (1982)).

For screening by hybridization, a DNA fragment from pYFC19 (Chang, et al., Infect. Immun., 55, p. 2348 (1987)) containing the 1ktCA genes was labeled with $^{32}$P-dATp and $^{32}$P-dCTP by nick translation. Filters were then washed twice with 2X SSC-0.1% SDS and twice with 0.2X SSC-0.1% SDS at room temperature. The final wash was with 0.16X SSC-0.1% SDS at 42° C. Plaques which gave positive signals with either method were picked, rescreened, and amplified on P2392.

SDS-PAGE and Western Blotting

SDS-PAGE was performed as previously described by Altman, et al. (*J. Bacterial,* 155, p. 1130 (1983)). Immunoreactive proteins were detected by Western blot analysis (Towbin et al., *Proc. Natl. Acad. Sci. USA* 76, 4350–4354 (1979)) as previously described (Chang, et al., *Infect. Immun.* 55, 2348–2354 (1987)). The first antibody was either bovine anti-leukotoxin (Chang et at., *Infect. Immun.* 55, 2348–2354 (1987)) or swine anti-hemolysin. Second antibodies to swine IgG were alkaline phosphatase conjugates purchased from Kirkegaard and Perry Laboratories, Gaithersburg, MD.

To analyze proteins expressed from the bacteriophage clones, 5 ml lysates were prepared and bacterial debris was removed by centrifugation. The cleared supernatants were then desalted and delipidated by chloroform-methanol extraction (Wessel et al., *Anal. Biochem.,* 138, p.141, (1984)). The denatured protein residue was collected by centrifugation and dissolved by boiling in SDS-PAGE sample buffer. Control lysates were prepared identically using the vector, Lambda-Dash. Cell free culture supernatants of *P. haemolytica, A. pleuropneumoniae* and *E. coli* harboring pSF4000 which expresses the complete hly determinant (Felmlee et al., J. Bacteriol. 163, 88–93 (1985)) were the sources for the leukotoxin and hemolysin antigen.

Southern Blotting

Aliquots of chromosomal DNA from *A. pleuropneumoniae* were digested separately with Pst I, Xba I, or Xho I, electrophoresed through a 0.7% agarose gel, and transferred to a nitrocellulose membrane as described (Southern, J. Mol. Biol., 98, p. 503 (1975)). The probe for hybridization was the 1.6 kbp Xba I fragment containing portions of the appC and appA genes from bacteriophage clone λyfc5 (FIG. 2). The blot was hybridized with the $^{32}$P-labeled probe in 4X SET (Mason and Williams, 1985) and 5X Denhardt's solution containing 100 g/ml denatured calf thymus DNA, 50 g/ml polyA, and 10 g/ml plyC at 65° C. for 12 hours. The filter was washed with 4X SET at room temperature and then sequentially with 4X SET, 2X SET, 1X SET, and 0.3X SET at 65° C.

DNA Sequencing and Analysis

DNA sequencing was performed by the di-deoxy chain termination method (Sanger et al., Proc. Natl. Acad. Sci. U.S.A., 74, p. 5463 (1977)). Appropriate regions from the *A. pleuropneumoniae* insert DNA in bacteriophage clones λyfc5 and λyfc12 were subcloned into the multiple cloning sites of the M13mp18 or M13mp19 and single stranded phage DNA was prepared by standard protocols (Messing, In *Methods Enzymol,* 101, p. 20, Academic Press (1983)). The sequencing reactions utilized $^{32}$P-dATp (800Ci/mol, New England Nuclear, Boston, MASS.), T7 DNA polymerase, and the commercially available Sequenase kit (United States Biochemicals, Cleveland, Ohio). Primers for DNA synthesis were the lac universal primer or other primers complementary to regions already sequenced. The latter were synthesized on an Applied Biosystems 380A DNA Synthesizer (Foster City, Calif.). Both strands of the cloned DNA were sequenced in their entirety. The DNA sequence was analyzed using the PCGene DNA and protein analysis programs (IntelliGenetics Crop., Mountain View, Calif.).

Assay of Hemolytic Activity

Aliquots of the indicated samples were incubated with a suspension of 0.2% goat erythrocytes in calcium-saline (10 mM $CaCl_2$, 0.85% NaCl, 10 mM Tris HC1, pH 7.5) for one hour at 37° C. At the end of the incubation, samples were centrifuged for 10 minutes at 500 g and the extent of hemolysis was estimated from the $A_{545}$ of the supernatant. The $A_{545}$ value corresponding to complete hemolysis was obtained by lysing the erythrocytes with Triton X-100. Background absorbance was measured for mixtures which were identical except that the erythrocytes were omitted. For antisera neutralization, samples were preincubated with 50 μ1 of the appropriate serum for one hour at room temperature.

Results

Cloning of the App Locus

Antibody screening with affinity purified antisera against the 110 kd antigen identified a single positive clone with an insert of 14 kb (FIG. 2). Screening the same library with DNA probes derived from pYFC19, a plasmid carrying the 1ktCA locus (Chang et al., 1987) identified eight clones (FIG. 2). The eight clones overlapped with each other and also with the clone isolated by immunological screening (FIG. 2). All but one of these 9 clones expressed a 110 kD polypeptide detected by Western blotting with the anti-App hemolysin antibody or the anti-leukotoxin antibody. One clone, λyfc5, produced a truncated polypeptide of 80K which was a truncated version of the 110 kD polypeptide. The fact that this clone expressed a truncated toxin provided a location and orientation for the putative App locus within the cloned DNA (FIG. 2).

Southern blot analysis using an Xba I fragment which maps to the toxin determinant as judged by DNA sequencing showed that no detectable rearrangement occurred during the cloning procedure. In addition, this analysis showed this sequence to be single copy in the *A. pleuropneumoniae* genome. Despite the fact that eight clones were identified which produced the full length hemolysin, no hemolytic activity could be detected in any of the phage lysates.

DNA Sequence of the appCA Genes

The region indicated by the truncated clone was subjected to DNA sequence analysis. The sequence of a 3.8 kb region is shown in FIG. 1. There is a small ORF of 159 codons encoding a polypeptide of 18.5 kD preceding the toxin reading frame, presumably the appC gene and a large ORF of 957 codons encoding a polypeptide of 10.5 kD, presumably the appA gene (FIG. 1).

The DNA sequence was screened for *E. coli* promoter-like sequences using the homology score method. There were three sequences which were similar to the TATAAT consensus promoter sequence (−10 region) and two sequences similar to the RNA polymerase-binding site, TTGACA (Reznikoff and Gold, In *Maximizing Gene Expression*, p. 1, Bostoni Butterworth publication (1986)) proximal to appC. The appC gene has two potential methionine start codons, each with a reasonable Shine-Dalgarno sequence located upstream. For simplicity, the first AUG codon was chosen as the appC gene start. A ribosome-binding site (Shine-Dalgarno sequence) upstream of the initiation codon of appA and a sequence very similar to the rho-independent transcriptional terminator of *E. coli* downstream of appA were also observed (FIG. 1). Such a potential termination sequence is found at an analogous location in the hemolysin and leukotoxin determinants of *E. coli* and *P. haemolytica*, respectively (Lo, et al., 1987; Highlander, et al., 1989; Welch and Pellet, 1988). The AppA protein also contains nine glycine-rich hexapeptide repeats near its carboxy-terminus. Similar repeats are found in the HlyA and LktA proteins (Strathdee and Lo, *J. Bacteriol.* 171, 916–928 (1987)) and are the basis of the RTX (repeat toxin) designation (Strathdee and Lo, 1989).

Expression of Hemolytic Activity in *E. coli*

The appA regions from bacteriophage clones λyfc7 and λyfc8 (FIG. 2) were subcloned into vector pHG165 (Stewart, et al., *Plasmid,* 15 p. 172, (1986)) as EcoRI-XhoI fragments yielding plasmids pYFC38 (appA) and pYFC37 (appCA), respectively. This strategy placed the appA gene of pYFC38 under the control of the lac promoter of the vector. The appCA genes of pYFC37 are likely to be expressed from an *A. pleuropneumoniae* promoter as well as the lac promoter of the vector. These plasmids were transformed into *E. coli* host, TB1, and the transformants were grown to early stationary phase and examined for the expression of the 110 kD protein and hemolytic activity. The 110 kD protein was expressed from both clones with antigen levels being considerably higher in transformants harboring pYFC38. However, hemolytic activity was only associated with the construct containing the intact appC gene.

This hemolytic activity, as is the case with the hemolysin secreted from *A. pleuropneumoniae*, could be neutralized with swine anti-App hemolysin antisera or rabbit antisera prepared against the *P. haemolytica* leukotoxin.

What is claimed is:

1. A purified isolated DNA sequence encoding *Actinobacillus pleuropneumoniae* hemolysin appCA products having the amino acid sequences shown in FIG. 1.

2. A purified isolated DNA sequence encoding the *A. pleuropneumoniae* appC product having the amino acid sequence shown in FIG. 1.

3. A purified isolated DNA sequence encoding the *A. pleuropneumoniae* hemolysin appA product having the amino acid sequence shown in FIG. 1.

4. The DNA sequence of claim 1, having the nucleotide sequence of bases 1–3386 shown in FIG. 1.

5. The DNA sequence of claim 2, having the nucleotide sequence of bases 1–477 shown in FIG. 1.

6. The DNA sequence of claim 3, having the nucleotide sequence of bases 519–3386 shown in FIG. 1.

7. A recombinant vector comprising the DNA sequence of claims 1, 2, 3, 4, 5, or 6.

8. The recombinant vector of claim 7 which is a recombinant plasmid.

9. The recombinant vector of claim 7 wherein the DNA sequence is operably linked to a strong promoter sequence.

10. A recombinant cell containing the vector of claim 7.

11. A recombinant cell containing the vector of claim 8.

12. A recombinant cell containing the vector of claim 9.

13. The recombinant cell of claim 10 which is a bacterial cell.

14. The recombinant cell of claim 11 which is a bacterial cell.

15. The recombinant cell of claim 12 which is a bacterial cell.

16. A method of producing *Actinobacillus pleuropneumoniae* app antigen comprising the steps of:

culturing recombinant cells, as defined in claim 10, under conditions which allow the cells to produce the antigen, and isolating the antigen from the culture.

17. The recombinant vector pYFC37 (ATCC 68135).

* * * * *